United States Patent
Bey et al.

(10) Patent No.: US 9,289,484 B2
(45) Date of Patent: Mar. 22, 2016

(54) **ATTENUATED *STREPTOCOCCUS SUIS* VACCINES AND METHODS OF MAKING AND USE THEREOF**

(71) Applicants: Russell F Bey, Arden Hills, MN (US); Paulraj Kirubakaran Lawrence, Worthington, MN (US); Randy R Simonson, Worthington, MN (US); Kamesh Reddy Sirigireddy, Sioux Falls, SD (US); Danielle A McKeown, Heron Lake, MN (US)

(72) Inventors: Russell F Bey, Arden Hills, MN (US); Paulraj Kirubakaran Lawrence, Worthington, MN (US); Randy R Simonson, Worthington, MN (US); Kamesh Reddy Sirigireddy, Sioux Falls, SD (US); Danielle A McKeown, Heron Lake, MN (US)

(73) Assignee: MERIAL, INC., Duluth, GA (US)

( * ) Notice: Subject to any disclaimer, the term of this patent is extended or adjusted under 35 U.S.C. 154(b) by 0 days.

(21) Appl. No.: 13/924,871

(22) Filed: Jun. 24, 2013

(65) Prior Publication Data

US 2014/0004144 A1 Jan. 2, 2014

Related U.S. Application Data

(60) Provisional application No. 61/664,935, filed on Jun. 27, 2012.

(51) Int. Cl.
*A61K 39/09* (2006.01)
*A61K 39/02* (2006.01)
*A61K 45/00* (2006.01)
*A61K 39/00* (2006.01)

(52) U.S. Cl.
CPC .............. *A61K 39/092* (2013.01); *A61K 39/09* (2013.01); *A61K 2039/522* (2013.01); *A61K 2039/542* (2013.01); *A61K 2039/552* (2013.01)

(58) Field of Classification Search
CPC ....... A61K 48/00; A61K 39/00; A61K 39/02; A61K 39/09; A61K 45/00
USPC .............. 424/93.1, 93.2, 93.44, 234.1, 235.1, 424/244.1, 278.1
See application file for complete search history.

(56) References Cited

U.S. PATENT DOCUMENTS

2001/0009668 A1 7/2001 Richardson

OTHER PUBLICATIONS

Lin, S.T., et al. "Studies on an attenuated haemolytic *Streptococcus suis* vaccine", Animal Husbandry and Veterinary Medicine, vol. 16, No. 3, pp. 103-106, 1984, Abstract Only.*

Allgaier, A., et al. 2001. Relatedness of *Streptococcus suis* isolates of various serotypes and clinical backgrounds as evaluated by macrorestriction analysis and expression of potential virulence traits. J. Clin. Microbiol. 39, 445-453.
Baums, C. G., et al., 2006. Identification of a novel virulence determinant with serum opacification activity in *Streptococcus suis*. Infect. Immun. 74, 6154-6162.
Baums, C.G., et al., 2009. *Streptococcus suis* bacterin and subunit vaccine immunogenicities and protective efficacies against serotypes 2 and 9. Clin Vaccince Immunol. 2, 200-208.
Berthelot-Herault, F., et al., 2005. Dilemma of virulence of *Streptococcus suis*: Canadian isolate 89-1591 characterized as a virulent strain using a standardized experimental model in pigs. Can. J. Vet. Res. 69, 236-240.
Cabot-Roy, G. et al., 2006. Phagocytosis and killing of *Streptococcus suis* by porcine neutrophils. Microb. Pathog. 41, 21-32.
Davidson A.L., et al., 2008. Structure, function, and evolution of bacterial ATP-binding cassette systems. Microbiol. Mol. Biol. Rev. 72, 317-364.
Davidson A.L., Chen J., 2004. ATP-binding cassette transporters in bacteria. Annu. Rev. Biochem 73, 241-268.
de Greeff, A., et al., 2002. Contribution of fibronectin-binding protein to pathogenesis of *Streptococcus suis* serotype 2. Infect. Immun. 70, 1319-1325.
Fittipaldi, N. et al. Potential use of an unencapsulated and aromatic amino acid-auxotrophic *Streptococcus suis* mutant as a live attenuated vaccine in swine. Vaccince 25 (2007) 3524-3535. Cited by ISR.
Fittipaldi, N. et al., 2008a. Significant contribution of the *pgdA* gene to the virulence of *Streptococcus suis*. Mol. Microbiol. 78, 1120-1135.
Fittipaldi, N. et al., 2008b. D-Alanylation of lipoteichoic acid contributes to the virulence of *Streptococcus suis*. Infect. Immun. 76, 3587-3594.
Fittipaldi, N. et al., 2011. Lineage and virulence of *Streptococcus suis* serotype 2 isolates from North America. Emerg Infect Dis. 12, 2239-2244.
Gottschalk, M. et al., 2007. *Streptococcus suis* infections in humans: the Chinese experience and the situation in North America. Anim. Health Res. Rev. 8, 29-45.
Henderson D.P., Payne, S.M., 1994. Vibrio cholerae iron transport system: roles of heme and siderophore iron transport in virulence and identification of a gene associated with multiple iron transport systems. Infect. Immun 62, 5120-5125.
Jacobs, A., et al., 1996. Protection of experimentally infected pigs by suilysin, the thiol-activated hemolysin of *Streptococcus suis*. Vet. Rec. 139, 225-228.
Li, Y., et al., 2007. Immunization with recombinant Sao protein confers protection against *Streptococcus suis* infection. Clin. Vaccine Immunol. 14, 937-943.

(Continued)

*Primary Examiner* — Rodney P Swartz
(74) *Attorney, Agent, or Firm* — Judy Jarecki-Black; Chad Kitchen; Merial, Inc.

(57) ABSTRACT

The present invention provides attenuated *S. suis* strains that elicit an immune response in animals against *S. suis*, compositions comprising said strains, methods of vaccination against *S. suis*, and kits for use with such methods and compositions. The invention further provides novel, mutagenically-induced mutations in *S. suis* genes, which are useful in the production of novel attenuated *S. suis* bacterial strains.

12 Claims, No Drawings

(56) References Cited

OTHER PUBLICATIONS

Poole, R.K., et al., 1994. The *cyD* gene product, component of a heterodimeric ABC transporter, is required for assembly of periplasmic cytochrome-c and of cytochrome-bd in *Escherichia coli*. FEMS Microbiol. Lett. 117, 217-224.

Poolman, B., et al., 2004. Bacterial osmosensing: roles of membrane structure and electrostatics in lipid-protein and protein-protein interactions. Biochim. Biophys. Acta 1666, 88-104.

Quessy, S., et al., 1995. Discrimination of virulent and avirulent *Streptococcus suis* capsular type 2 isolates from different geographical origins. Infect. Immun. 63, 1975-1979.

Kock et al. Iintranasal immunization with a live *Streptococcus suis* isogenic *ofs* mutant elicited suilysin-neutralization titers but failed to induce opsonizing antibodies and protection. Veterinary Immunology and Immunopathology 132 (2009) 135-145.

XP002712926 WPI Reference—cited by ISR.

XP002507758—Hasebrouck et al. Efficacy of vaccines against bacterial diseases in swine: what can we expect? Veterinary Microbiology 100 (2004) 255-268. Cited by ISR.

XP002712927 Accession # G7S294. Cited by ISR.

XP002712928 Accession # CSVVX4. Cited by ISR.

XP002712929 Accession # EBUQ69. Cited by ISR.

* cited by examiner

ATTENUATED *STREPTOCOCCUS SUIS* VACCINES AND METHODS OF MAKING AND USE THEREOF

INCORPORATION BY REFERENCE

This application claims priority to provisional application U.S. Ser. No. 61/664,935, filed on Jun. 27, 2012, and incorporated by reference herein in its entirety.

FIELD OF THE INVENTION

The present invention relates generally to attenuated bacterial vaccines, particularly those providing broad, safe, and effective protection to porcines against infections/disease caused by *Streptococcus suis*. The invention further relates to methods of producing the attenuated bacteria, and to the identification of nucleic acid variations that are associated with decreased virulence of the attenuated bacteria.

The invention accordingly relates to immunogenic or vaccine compositions comprising the bacteria of the invention; e.g., live attenuated bacteria. The bacteria also could be inactivated in the compositions; but it may be advantageous that the bacteria are live attenuated *S. suis* bacteria. The invention therefore further relates to methods for preparing and/or formulating such compositions; e.g., culturing or growing or propagating the bacteria on or in suitable medium, harvesting the bacteria, optionally inactivating the bacteria, and optionally admixing the bacteria with a suitable veterinarily or pharmaceutically acceptable carrier, excipient, diluent or vehicle and/or an adjuvant and/or stabilizer. Thus, the invention also relates to the use of the bacteria in formulating such compositions.

BACKGROUND OF THE INVENTION

*Streptococcus suis* is a Gram positive cocci that predominantly colonizes pigs. While the adult pigs serve as asymptomatic carries, it can cause fatal meningitis, septicemia arthritis and bronchopneumonia in piglets. Adult pigs usually carry *S. suis* as commensal in their tonsillar crypts and upper respiratory tracts, but bacteria have also been isolated from the gastrointestinal and genital tracts. Almost all the adult pigs serve as reservoirs for *S. suis* and this pathogen affects pig industries worldwide.

In addition *S. suis* also colonizes a wide variety of mammalian and avian species [Gottschalk et al., 2007]. Furthermore, *S. suis* is an important zoonotic agent [Perch et al., 1968], although human infections with *S. suis* are rare in Europe and North America. Most of these cases in North America and Europe are almost exclusively related to occupational exposure to pigs or pork products. However, the incidences of human infection with *S. suis* are greater in S.E. Asia and China. Although meningitis is the most common manifestation in humans, occasionally septicemia and endocarditis are also seen.

Out of the 33 known *S. suis* serotypes, serotype 2 is most frequently associated with meningitis and arthritis in pigs from North America and Europe [Fittipaldi et al., 2009; Higgins and Gottschalk, 2006]. The various *S. suis* virulence factors include; capsule, fibronectin/fibrinogen binding protein, serum opacity-like factor and modifications of the cell wall lipoteichoic acids and peptidoglycan [Baums et al., 2006; Chabot-Roy et al., 2006; de Greeff et al., 2002; Fittipaldi et al., 2008a, b; Smith et al., 1999]. Furthermore, the virulence factors shared among various strains of the same serotype show a wide variation [Berthelot-Herault et al., 2005; Quessy et al., 1995; Vecht et al., 1992]. The phenotypic markers for *S. suis* virulence include the hemolysis factor, suilysin (encoded by sly), LPXTG-protein known as muramidase-released protein [MRP, 136 kDa, encoded by gene mrp] and the secreted protein extracellular factor [EF, 110 kDa, encoded by gene epf].There is a strong positive correlation between the presence of these virulence proteins and virulent phenotypes in Eurasian strains of *S. suis* [Gottschalk et al., 2007; Vecht et al., 1991]. In these continents, serotype 2 MRP$^+$EF$^+$SLY$^+$ strains are mainly isolated from diseased pigs showing severe clinical signs of disease while MRP$^-$EF$^-$SLY$^-$ strains have been frequently isolated from healthy pigs [Allgaier et al., 2001; Vecht et al., 1992].

Whole cells and numerous *S. suis* proteins have been investigated as potential vaccine candidates. Immunization with a wild type bacterin completely protected against challenge with the homologous serotype while non-encapsulated mutant failed to afford protection [Wisselink et al., 2002]. In a study conducted by Li et al, recombinant SAO (*S. suis* surface protein) in combination with QuilA protected against *S. suis* serotype 2 disease in pigs. Intramuscular immunization with SAO elicited significant humoral antibody responses, but were predominantly IgG2. Recombinant SAO immunization also induced opsonophagocytic antibodies [Li et al., 2007]. Immunization of piglets with purified suilysin from *S. suis* strain P1/7 (serotype 2), increased neutralizing antibody titers suggesting that SLY might function as protective antigen [Jacobs et al., 1996]. However, none of these experiments used heterologous serotypes to challenge pigs vaccinated with these antigens. In a study by Baums et al, *S. suis*, serotype 2 bacterin induced protective immunity against homologous challenge. In contrast, the protective efficacy of the MAP subunit vaccine was low, although MAP immunization resulted in high serum IgG2 titers against MRP and SAO. Importantly, immunization with bacterin but not with MAP induced opsonizing antibody titers against the serotype 2 strain, and these antibody titers were found to correlate with protection. However, after absorption with a non-encapsulated isogenic mutant, the sera from bacterin-immunized piglets failed to facilitate neutrophil killing, indicating that antibodies directed against capsule may not have been essential for opsonophagocytosis [Baums et al., 2009]. Furthermore, induction of opsonizing antibodies against serotype 9 was not detectable in the group receiving bacterin or in the group receiving the MAP vaccine, resulting in low protection against serotype 9 strains.

None of the vaccination-challenge studies have yielded a broadly protective vaccine against *S. suis* infections. Furthermore, the knowledge about the precise understanding of *S. suis* pathogenesis at molecular level is fragmented due to the arsenal of virulence factors among strains within a serotype and complex molecular mechanism involved in interacting with its host. Lack of an effective vaccine against *S. suis* infections is a major problem in modern swine production. Thus, it a primary object of the instant disclosure to provide a safe and effective *S. suis* vaccine.

SUMMARY OF THE INVENTION

An object of this invention is to provide attenuated vaccines as well as methods for treatment and prophylaxis of infection by *S. suis*.

The present invention further relates to new attenuated strains of *S. suis*, which provide safe, effective, and broad protective immunity. Relative to a parent *S. suis* strain, the attenuated strains may have one or more polymorphic variant nucleotides, whose presence is associated with reduced virulence.

The invention provides a mutant bacterium comprising a mutation(s) in one or more nucleic acids sequences, relative to the wild type/parental bacterium, which renders the mutant bacterium attenuated, relative to the parent bacterium, which parent bacterium comprises nucleic acids encoding wild type proteins having peptide sequences as set forth in SEQ ID NOs:2, 6, and 10. In a particular embodiment, the mutant bacterium comprises nucleic acid sequences as set forth in SEQ ID NOs:3, 7, and 11, which encode for peptides as set forth in SEQ ID NOs:4, 8, and 12, and which cause the mutant bacterium to be attenuated/non-virulent, relative to the virulent wild type/parental bacterium. In another embodiment, the mutant bacterium has other mutations in wild type peptides as set forth in SEQ ID NOs:2, 6, and 10 (i.e. other than those yielding peptides as set forth in SEQ ID NOs:4, 8, and 12), which result in the mutant bacterium being attenuated relative to the wild type/parent strain.

According to one particular embodiment, the strains may have "alternative forms of genes", which are defined herein as "alleles", relative to their parent *S. suis* strain. In an embodiment, the alternative alleles are responsible for reduced or attenuated virulence. As defined herein, the term "gene" will be used in a broad sense, and shall encompass both coding and non-coding sequences (i.e. upstream and downstream regulatory sequences, promoters, 5'/3' UTR, introns, and exons). Where reference to only a gene's coding sequence is intended, the term "gene's coding sequence" or "CDS" will be used interchangeably throughout this disclosure.

In a particular embodiment, the attenuated strains have one or more polymorphism(s) in a rpsL-S12 (a 30S ribosomal subunit protein), an ABC transporter ATP binding membrane protein (ABC-ATPBMP), and bacterial transcription regulator (marR), all three or combinations thereof. In an embodiment, there are at least 4 nucleotide differences between an attenuated strain and its parent strain: 2 SNPs in the rpsL-S12 and 1 SNP in the ABC-ATPBMP and marR.

According to another aspect, the present invention relates to genetically-modified *S. suis* strains, wherein expression of rpsL-S12, ABC-ATPBMP, and marR or all three, is altered relative to the parent *S. suis* strain, resulting in reduced virulence of the genetically-modified strain.

According to another aspect, the present invention relates to a method for producing an attenuated *S. suis* bacterium, comprising the steps of:

(a) growing a *S. suis* parent strain in the presence of a mutagenic agent;

(b) seeding surviving cells to an appropriate medium;

(c) testing individual colonies by injecting into pigs to determine virulence;

(d) determining the strain is attenuated if the pigs do not present with clinical signs that are associated with infection by the parental strain.

In one embodiment, the attenuated vaccines further comprises an adjuvant. The adjuvant may be any substance which increases and/or augments the elicited immune response, as compared to attenuated vaccine alone. Mucosal adjuvants, including chitosans and derivatives thereof, are particularly useful for the disclosed oral attenuated vaccines.

The invention further provides methods for inducing an immunological (or immunogenic) or protective response against *S. suis*, as well as methods for preventing or treating *S. suis*, or disease state(s) caused by *S. suis*, comprising administering the attenuated bacteria, or a composition comprising the attenuated bacteria to animals in need thereof.

Kits comprising at least the attenuated *S. suis* strain and instructions for use are also provided.

These and other embodiments are disclosed or are obvious from and encompassed by, the following Detailed Description.

DETAILED DESCRIPTION OF THE INVENTION

The present invention provides nucleotide sequences and genes involved in the attenuation of a microorganism, such as bacteria, for instance, Gram positive bacteria, e.g., *Streptococcus suis* (*S. suis*), products (e.g., proteins, antigens, immunogens, epitopes) encoded by the nucleotide sequences, methods for producing such nucleotide sequences, products, micro-organisms, and uses therefor, such as for preparing vaccine or immunogenic compositions or for eliciting an immunological or immune response or as a vector, e.g., as an expression vector (for instance, an in vitro or in vivo expression vector).

Mutations introduced into nucleotide sequences and genes of micro-organisms produce novel and nonobvious attenuated mutants. These mutants are useful for the production of live attenuated immunogenic compositions or live attenuated vaccines having a high degree of immunogenicity.

These mutants are also useful as vectors which can be useful for expression in vitro of expression products, as well as for reproduction or replication of nucleotide sequences (e.g., replication of DNA), and for in vivo expression products.

Identification of the mutations provides novel and nonobvious nucleotide sequences and genes, as well as novel and nonobvious gene products encoded by the nucleotide sequences and genes.

Such gene products provide antigens, immunogens and epitopes, and are useful as isolated gene products.

Such isolated gene products, as well as epitopes thereof, are also useful for generating antibodies, which are useful in diagnostic applications.

Such gene products, which can provide or generate epitopes, antigens or immunogens, are also useful for immunogenic or immunological compositions, as well as vaccines.

In an aspect, the invention provides bacteria containing an attenuating mutation in a nucleotide sequence or a gene wherein the mutation modifies, reduces or abolishes the expression and/or the biological activity of a polypeptide or protein encoded by a gene, resulting in attenuated virulence of the bacterium.

The mutation is not necessarily located within a coding sequence or gene to disrupt its function, leading to attenuation. The mutation can also be made in nucleotide sequences involved in the regulation of the expression of the gene, for instance, in regions that regulate transcription initiation, translation and transcription termination. Thus also included are promoters and ribosome binding regions (in general these regulatory elements lie approximately between 60 and 250 nucleotides upstream of the start codon of the coding sequence or gene; Doree S M et al., J. Bacteriol. 2001, 183(6): 1983-9; Pandher K et al., Infect. Imm. 1998, 66(12): 5613-9; Chung J Y et al., FEMS Microbiol letters 1998, 166: 289-296), transcription terminators (in general the terminator is located within approximately 50 nucleotides downstream of the stop codon of the coding sequence or gene; Ward C K et al., Infect. Imm. 1998, 66(7): 3326-36). In the case of an operon, such regulatory regions may be located in a greater distance upstream of the gene or coding sequence. A mutation in an intergenic region can also lead to attenuation.

A mutation within such regulatory sequences associated with the coding sequence or gene so that the mutation of this nucleotide sequence modifies, inhibits or abolishes the expression and/or the biological activity of the polypeptide or the protein encoded by the gene, resulting in attenuated virulence of the bacterium would be an equivalent to a mutation within a gene or coding sequence identified in the present invention Attenuation reduces or abolishes the pathogenicity of the bacteria and the gravity of the clinical signs or lesions, decreases the growth rate of the bacteria, and prevents the death from the bacteria.

In particular, the present invention encompasses attenuated *S. suis* strains and vaccines comprising the same, which elicit an immunogenic response in an animal, particularly the attenuated *S. suis* strains that elicit, induce or stimulate a response in a porcine.

Particular *S. suis* attenuated strains of interest have mutations in genes, relative to wild type virulent parent strain, which are associated with virulence. It is recognized that, in addition to strains having the disclosed mutations, attenuated strains having any number of mutations in the disclosed virulence genes can be used in the practice of this invention.

In an embodiment, the attenuated strains comprise nucleic acid sequences comprising the nucleotides as set forth in SEQ ID NOs:3, 7, 11, or combinations thereof. At the time of this disclosure, these sequences were not known to exist in any naturally-occurring *S. suis* genomes, and were only produced as a result of inventor's mutagenesis methods, which had been performed on the virulent parental strain, wherein the wild type genes comprised the nucleotides as set forth in SEQ ID NOs:1, 5, and 9.

In another embodiment, the attenuated *S. suis* strains comprise nucleic acids encoding peptides having the sequence as set forth in SEQ ID NOs:4, 8, 12 or combinations thereof. In yet another embodiment, the strains comprise nucleic acids encoding peptides having at least one amino acid substitution with respect to the sequences as set forth in SEQ ID NOs:2, 6, 10 or combinations thereof. In an embodiment, the substitution is as outlined in Table 1 (for the vaccine strain).

In yet another embodiment, the attenuated *S. suis* strain has mutations in the same genes, relative to its virulent parental strain, as the strain deposited at the ATCC under the Patent Deposit Designation PTA-13269. These mutations result in the attenuated strain having reduced virulence relative to it virulent parental strain.

In a particular embodiment, the attenuated strain is the strain deposited at the ATCC under the Patent Deposit Designation PTA-13269.

In another aspect, the novel attenuated *S. suis* strains are formulated into safe, effective vaccine against *S. suis* and infections/diseases cause by *S. suis*.

In an embodiment, the *S. suis* vaccines further comprise an adjuvant. In a particular embodiment, the adjuvant is a mucosal adjuvant, such as chitosan, methylated chitosan, trimethylated chitosan, or derivatives or combinations thereof.

In an embodiment, the adjuvant comprises whole bacteria and/or viruses, including *H. parasuis*, clostridium, swine influenza virus (SIV), porcine circovirus (PCV), porcine reproductive and respiratory syndrome virus (PRRSV), *Mannheimia*, *Pasteurella*, *Histophilus*, *Salmonella*, *Escherichia coli*, or combinations and/or variations thereof. In several embodiments, the adjuvant increases the animal's production of IgM, IgG, IgA, and/or combinations thereof.

By "antigen" or "immunogen" means a substance that induces a specific immune response in a host animal. The antigen may comprise a whole organism, killed, attenuated or live; a subunit or portion of an organism; a recombinant vector containing an insert with immunogenic properties; a piece or fragment of DNA capable of inducing an immune response upon presentation to a host animal; a polypeptide, an epitope, a hapten, or any combination thereof. Alternately, the immunogen or antigen may comprise a toxin or antitoxin.

The terms "protein", "peptide", "polypeptide" and "polypeptide fragment" are used interchangeably herein to refer to polymers of amino acid residues of any length. The polymer can be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component.

The term "immunogenic or antigenic polypeptide" as used herein includes polypeptides that are immunologically active in the sense that once administered to the host, it is able to evoke an immune response of the humoral and/or cellular type directed against the protein. Preferably the protein fragment is such that it has substantially the same immunological activity as the total protein. Thus, a protein fragment according to the invention comprises or consists essentially of or consists of at least one epitope or antigenic determinant. An "immunogenic" protein or polypeptide, as used herein, includes the full-length sequence of the protein, analogs thereof, or immunogenic fragments thereof. By "immunogenic fragment" is meant a fragment of a protein which includes one or more epitopes and thus elicits the immunological response described above. Such fragments can be identified using any number of epitope mapping techniques, well known in the art. See, e.g., Epitope Mapping Protocols in Methods in Molecular Biology, Vol. 66 (Glenn E. Morris, Ed., 1996). For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al., 1984; Geysen et al., 1986. Similarly, conformational epitopes are readily identified by determining spatial conformation of amino acids such as by, e.g., x-ray crystallography and 2-dimensional nuclear magnetic resonance. See, e.g., Epitope Mapping Protocols, supra. Methods especially applicable to the proteins of *T. parva* are fully described in PCT/US2004/022605 incorporated herein by reference in its entirety.

As discussed herein, the invention encompasses active fragments and variants of the antigenic polypeptide. Thus, the term "immunogenic or antigenic polypeptide" further contemplates deletions, additions and substitutions to the sequence, so long as the polypeptide functions to produce an immunological response as defined herein. The term "conservative variation" denotes the replacement of an amino acid residue by another biologically similar residue, or the replacement of a nucleotide in a nucleic acid sequence such that the encoded amino acid residue does not change or is another biologically similar residue. In this regard, particularly preferred substitutions will generally be conservative in nature, i.e., those substitutions that take place within a family of amino acids. For example, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar— glycine, asparagine, glutamine, cystine, serine, threonine, tyrosine. Phenylalanine, tryptophan, and tyrosine are sometimes classified as aromatic amino acids. Examples of conservative variations include the substitution of one hydrophobic residue such as isoleucine, valine, leucine or methionine for another hydrophobic residue, or the substitution of one polar residue for another polar residue, such as the substitution of arginine for lysine, glutamic acid for aspartic acid, or glutamine for asparagine, and the like; or a similar conservative replacement of an amino acid with a structurally related amino acid that will not have a major effect on the biological activity. Proteins having substantially the same amino acid sequence as the reference molecule but possessing minor amino acid substitutions that do not substantially affect the immunogenicity of the protein are, therefore, within the definition of the reference polypeptide. All of the polypeptides produced by these modifications are included herein. The term "conservative variation" also includes the use of a substituted amino acid in place of an unsubstituted parent amino acid provided that antibodies raised to the substituted polypeptide also immunoreact with the unsubstituted polypeptide.

The term "epitope" refers to the site on an antigen or hapten to which specific B cells and/or T cells respond. The term is also used interchangeably with "antigenic determinant" or "antigenic determinant site". Antibodies that recognize the same epitope can be identified in a simple immunoassay showing the ability of one antibody to block the binding of another antibody to a target antigen.

An "immunological response" to a composition or vaccine is the development in the host of a cellular and/or antibody-mediated immune response to a composition or vaccine of interest. Usually, an "immunological response" includes but is not limited to one or more of the following effects: the production of antibodies, B cells, helper T cells, and/or cytotoxic T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction or lack of symptoms and/or clinical disease signs normally displayed by an infected host, a quicker recovery time and/or a lowered viral titer in the infected host.

By "animal" is intended mammals, birds, and the like. Animal or host as used herein includes mammals and human. The animal may be selected from the group consisting of equine (e.g., horse), canine (e.g., dogs, wolves, foxes, coyotes, jackals), feline (e.g., lions, tigers, domestic cats, wild cats, other big cats, and other felines including cheetahs and lynx), ovine (e.g., sheep), bovine (e.g., cattle), porcine (e.g., pig), avian (e.g., chicken, duck, goose, turkey, quail, pheasant, parrot, finches, hawk, crow, ostrich, emu and cassowary), primate (e.g., prosimian, tarsier, monkey, gibbon, ape), ferrets, seals, and fish. The term "animal" also includes an individual animal in all stages of development, including newborn, embryonic and fetal stages.

Unless otherwise explained, all technical and scientific terms used herein have the same meaning as commonly understood by one of ordinary skill in the art to which this disclosure belongs. The singular terms "a", "an", and "the" include plural referents unless context clearly indicates otherwise. Similarly, the word "or" is intended to include "and" unless the context clearly indicate otherwise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

Compositions

The present invention relates to a *S. suis* vaccine or composition which may comprise an attenuated *S. suis* strain and a pharmaceutically or veterinarily acceptable carrier, excipient, or vehicle, which elicits, induces or stimulates a response in an animal.

The term "nucleic acid" and "polynucleotide" refers to RNA or DNA that is linear or branched, single or double stranded, or a hybrid thereof. The term also encompasses RNA/DNA hybrids. The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes and primers. A polynucleotide may comprise modified nucleotides, such as methylated nucleotides and nucleotide analogs, uracyl, other sugars and linking groups such as fluororibose and thiolate, and nucleotide branches. The sequence of nucleotides may be further modified after polymerization, such as by conjugation, with a labeling component. Other types of modifications included in this definition are caps, substitution of one or more of the naturally occurring nucleotides with an analog, and introduction of means for attaching the polynucleotide to proteins, metal ions, labeling components, other polynucleotides or solid support. The polynucleotides can be obtained by chemical synthesis or derived from a microorganism.

The term "gene" is used broadly to refer to any segment of polynucleotide associated with a biological function. Thus, genes include introns and exons as in genomic sequence, or just the coding sequences as in cDNAs and/or the regulatory sequences required for their expression. For example, gene also refers to a nucleic acid fragment that expresses mRNA or functional RNA, or encodes a specific protein, and which includes regulatory sequences.

An "isolated" biological component (such as a nucleic acid or protein or organelle) refers to a component that has been substantially separated or purified away from other biological components in the cell of the organism in which the component naturally occurs, for instance, other chromosomal and extra-chromosomal DNA and RNA, proteins, and organelles. Nucleic acids and proteins that have been "isolated" include nucleic acids and proteins purified by standard purification methods. The term also embraces nucleic acids and proteins prepared by recombinant technology as well as chemical synthesis.

The term "conservative variation" denotes the replacement of an amino acid residue by another biologically similar residue, or the replacement of a nucleotide in a nucleic acid sequence such that the encoded amino acid residue does not change or is another biologically similar residue. In this regard, particularly preferred substitutions will generally be conservative in nature, as described above.

The term "recombinant" means a polynucleotide with semisynthetic, or synthetic origin which either does not occur in nature or is linked to another polynucleotide in an arrangement not found in nature.

"Heterologous" means derived from a genetically distinct entity from the rest of the entity to which it is being compared. For example, a polynucleotide may be placed by genetic engineering techniques into a plasmid or vector derived from a different source, and is a heterologous polynucleotide. A promoter removed from its native coding sequence and operatively linked to a coding sequence other than the native sequence is a heterologous promoter.

The polynucleotides of the invention may comprise additional sequences, such as additional encoding sequences within the same transcription unit, controlling elements such as promoters, ribosome binding sites, 5'UTR, 3'UTR, transcription terminators, polyadenylation sites, additional transcription units under control of the same or a different promoter, sequences that permit cloning, expression, homologous recombination, and transformation of a host cell, and any such construct as may be desirable to provide embodiments of this invention.

Methods of use and Article of Manufacture

The present invention includes the following method embodiments. In an embodiment, a method of vaccinating an animal comprising administering a composition comprising an attenuated S. suis strain and a pharmaceutical or veterinarily acceptable carrier, excipient, or vehicle to an animal is disclosed. In one aspect of this embodiment, the animal is a porcine.

In one embodiment of the invention, a prime-boost regimen can be employed, which is comprised of at least one primary administration and at least one booster administration using at least one common polypeptide, antigen, epitope or immunogen. Typically the immunological composition or vaccine used in primary administration is different in nature from those used as a booster. However, it is noted that the same composition can be used as the primary administration and the booster administration. This administration protocol is called "prime-boost".

A prime-boost regimen comprises at least one prime-administration and at least one boost administration using at least one common polypeptide and/or variants or fragments thereof. The vaccine used in prime-administration may be different in nature from those used as a later booster vaccine. The prime-administration may comprise one or more administrations. Similarly, the boost administration may comprise one or more administrations.

The dose volume of compositions for target species that are mammals, e.g., the dose volume of pig or swine compositions, based on bacterial antigens, is generally between about 0.1 to about 2.0 ml, between about 0.1 to about 1.0 ml, and between about 0.5 ml to about 1.0 ml.

The efficacy of the vaccines may be tested about 2 to 4 weeks after the last immunization by challenging animals, such as porcine, with a virulent strain of S. suis. Both homologous and heterologous strains are used for challenge to test the efficacy of the vaccine. The animal may be challenged by IM or SC injection, spray, intra-nasally, intra-ocularly, intra-tracheally, and/or orally. Samples from joints, lungs, brain, and/or mouth may be collected before and post-challenge and may be analyzed for the presence of S. suis-specific antibody.

The compositions comprising the attenuated bacterial strains of the invention used in the prime-boost protocols are contained in a pharmaceutically or veterinary acceptable vehicle, diluent or excipient. The protocols of the invention protect the animal from S. suis and/or prevent disease progression in an infected animal.

The various administrations are preferably carried out 1 to 6 weeks apart. Preferred time interval is 3 to 5 weeks, and optimally 4 weeks according to one embodiment, an annual booster is also envisioned. The animals, for example pigs, may be at least 3-4 weeks of age at the time of the first administration.

It should be understood by one of skill in the art that the disclosure herein is provided by way of example and the present invention is not limited thereto. From the disclosure herein and the knowledge in the art, the skilled artisan can determine the number of administrations, the administration route, and the doses to be used for each injection protocol, without any undue experimentation.

Another embodiment of the invention is a kit for performing a method of eliciting or inducing an immunological or protective response against S. suis in an animal comprising an attenuated S. suis immunological composition or vaccine and instructions for performing the method of delivery in an effective amount for eliciting an immune response in the animal.

Another embodiment of the invention is a kit for performing a method of inducing an immunological or protective response against S. suis in an animal comprising a composition or vaccine comprising an attenuated S. suis strain of the invention, and instructions for performing the method of delivery in an effective amount for eliciting an immune response in the animal.

Yet another aspect of the present invention relates to a kit for prime-boost vaccination according to the present invention as described above. The kit may comprise at least two vials: a first vial containing a vaccine or composition for the prime-vaccination according to the present invention, and a second vial containing a vaccine or composition for the boost-vaccination according to the present invention. The kit may advantageously contain additional first or second vials for additional prime-vaccinations or additional boost-vaccinations.

The pharmaceutically or veterinarily acceptable carriers or vehicles or excipients are well known to the one skilled in the art. For example, a pharmaceutically or veterinarily acceptable carrier or vehicle or excipient can be a 0.9% NaCl (e.g., saline) solution or a phosphate buffer. Other pharmaceutically or veterinarily acceptable carrier or vehicle or excipients that can be used for methods of this invention include, but are not limited to, poly-(L-glutamate) or polyvinylpyrrolidone. The pharmaceutically or veterinarily acceptable carrier or vehicle or excipients may be any compound or combination of compounds facilitating the administration of the vector (or protein expressed from an inventive vector in vitro); advantageously, the carrier, vehicle or excipient may facilitate transfection and/or improve preservation of the vector (or protein). Doses and dose volumes are herein discussed in the general description and can also be determined by the skilled artisan from this disclosure read in conjunction with the knowledge in the art, without any undue experimentation.

The immunological compositions and vaccines according to the invention may comprise or consist essentially of one or more adjuvants. Suitable adjuvants for use in the practice of the present invention are (1) polymers of acrylic or methacrylic acid, maleic anhydride and alkenyl derivative polymers, (2) immunostimulating sequences (ISS), such as oligodeoxyribonucleotide sequences having one or more non-methylated CpG units (Klinman et al., 1996; WO98/16247), (3) an oil in water emulsion, such as the SPT emulsion described on page 147 of "Vaccine Design, The Subunit and Adjuvant Approach" published by M. Powell, M. Newman, Plenum Press 1995, and the emulsion MF59 described on page 183 of the same work, (4) cationic lipids containing a quaternary ammonium salt, e.g., DDA (5) cytokines, (6) aluminum hydroxide or aluminum phosphate, (7) saponin or (8) other adjuvants discussed in any document cited and incorporated by reference into the instant application, or (9) any combinations or mixtures thereof.

In an embodiment, adjuvants include those which promote improved absorption through mucosal linings. Some examples include MPL, LTK63, toxins, PLG microparticles and several others (Vajdy, M. Immunology and Cell Biology (2004) 82, 617-627). In an embodiment, the adjuvant may be a chitosan (Van der Lubben et al. 2001; Patel et al. 2005; Majithiya et al. 2008; U.S. Pat. No. 5,980.912).

In an embodiment, the adjuvant may be inactivated bacteria, an inactivated virus, fractions of inactivated bacteria, bacterial lipopolysaccharides, bacterial toxins, or derivatives or combinations thereof.

In an embodiment, the adjuvant comprises whole bacteria and/or viruses, including *H. parasuis*, clostridium, swine immunodeficiency virus (SIV), porcine circovirus (PCV), porcine reproductive and respiratory syndrome virus (PRRSV), *Mannheimia, Pasteurella, Histophilus, Salmonella, Escherichia coli*, or combinations and/or variations thereof. In several embodiments, the adjuvant increases the animal's production of IgM, IgG, IgA, and/or combinations thereof.

References:

1. Allgaier, A., et al. 2001. Relatedness of *Streptococcus suis* isolates of various serotypes and clinical backgrounds as evaluated by macrorestriction analysis and expression of potential virulence traits. J. Clin. Microbiol. 39, 445-453.
2. Baums, C. G., et al., 2006. Identification of a novel virulence determinant with serum opacification activity in *Streptococcus suis*. Infect. Immun. 74, 6154-6162.
3. Baums, C. G., et al., 2009. *Streptococcus suis* bacterin and subunit vaccine immunogenicities and protective efficacies against serotypes 2 and 9.Clin Vaccine Immunol. 2, 200-208.
4. Berthelot-Herault, F., et al., 2005. Dilemma of virulence of *Streptococcus suis*: Canadian isolate 89-1591 characterized as a virulent strain using a standardized experimental model in pigs. Can. J. Vet. Res. 69, 236-240.
5. Chabot-Roy, G. et al., 2006. Phagocytosis and killing of *Streptococcus suis* by porcine neutrophils. Microb. Pathog. 41, 21-32.
6. Davidson A. L., et al., 2008. Structure, function, and evolution of bacterial ATP-binding cassette systems". Microbiol. Mol. Biol. Rev. 72, 317-364.
7. Davidson A. L., Chen J., 2004. ATP-binding cassette transporters in bacteria". Annu Rev. Biochem 73, 241-268.
8. de Greeff, A., et al., 2002. Contribution of fibronectin-binding protein to pathogenesis of *Streptococcus suis* serotype 2. Infect. Immun. 70, 1319-1325.
9. Fittipaldi, N. et al., 2008a. Significant contribution of the pgdA gene to the virulence of *Streptococcus suis*. Mol. Microbiol. 78, 1120-1135.
10. Fittipaldi, N. et al., 2008b. D-Alanylation of lipoteichoic acid contributes to the virulence of *Streptococcus suis*. Infect. Immun. 76, 3587-3594.
11. Fittipaldi, N. et al., 2011. Lineage and virulence of *Streptococcus suis* serotype 2 isolates from North America. Emerg Infect Dis. 12, 2239-2244.
12. Gottschalk, M. et al., 2007. *Streptococcus suis* infections in humans: the Chinese experience and the situation in North America. Anim. Health Res. Rev. 8, 29-45.
13. Henderson D. P., Payne, S. M., 1994. *Vibrio cholerae* iron transport system: roles of heme and siderophore iron transport in virulence and identification of a gene associated with multiple iron transport systems". Infect. Immun 62, 5120-5125.
14. Higgins, R., Gottschalk, M., 2006. Streptococcocal diseases. In: Straw, B. E., D'Allaire, S., Mengeling, W. L., Taylor, D. J. (Eds.), Diseases of Swine. Blackwell Publishing, pp. 769-783.
15. Jacobs, A., et al., 1996. Protection of experimentally infected pigs by suilysin, the thiol-activated hemolysin of *Streptococcus suis*. Vet. Rec. 139, 225-228.
16. Li, Y., et al., 2007. Immunization with recombinant Sao protein confers protection against *streptococcus suis* infection. Clin. Vaccine Immunol. 14, 937-943.
17. McEvoy, G. K., editor. 1989. AHFS Drug information 89. Bethesda, Md.: American Society of Hospital Pharmacists, 1925-1927.
18. Perch, B., et al., 1968. Group R streptococci pathogenic for man. Two cases of meningitis and one fatal case of sepsis. Acta Pathol Microbiol Scand 74, 69-76.
19. Poole, R. K., et al., 1994. The cydD gene product, component of a heterodimeric ABC transporter, is required for assembly of periplasmic cytochrome-c and of cytochrome-bd in *Escherichia coli*". FEMS Microbiol. Lett. 117, 217-224.
20. Poolman, B., et al., 2004. Bacterial osmosensing: roles of membrane structure and electrostatics in lipid-protein and protein-protein interactions". Biochim. Biophys. Acta 1666, 88-104.
21. Quessy, S., et al., 1995. Discrimination of virulent and avirulent *Streptococcus suis* capsular type 2 isolates from different geographical origins. Infect. Immun. 63, 1975-1979.
22. Smith, H. E., et al., 1999. Identification and characterization of the cps locus of *Streptococcus suis* serotype 2: the capsule protects against phagocytosis and is an important virulence factor. Infect. Immun. 67, 1750-1756.
23. Sinha, R. P., 1977. Acriflavine-Resistant Mutant of *Streptococcus cremoris*. Antimicro and Chemo 12, 383-389.
24. Vecht, U. et al., 1991. Identification of two proteins associated with virulence of *Streptococcus suis* type 2. Infect. Immun. 59, 3156-3162.
25. Vecht, U. et al., 1992. Virulence of *Streptococcus suis* type 2 strains in newborn germfree pigs depends on phenotype. Infect. Immun. 60, 550-556.
26. Wisselink, H. J., et al., 2002. Assessment of protective efficacy of live and killed vaccines based on a non-encapsulated mutant of *Streptococcus suis* serotype 2. Vet. Microbiol. 84, 155-168.
27. Zhou, Z. M., et al., 1998. Function of *Escherichia coli* MsbA, an essential ABC family transporter, in lipid A and phospholipid biosynthesis". J. Biol. Chem. 273,12466-12475.
28. George, A. M., and S. B. Levy. 1983. Gene in the major cotransduction gap of the *Escherichia coli* K-12 linkage map required for the expression of chromosomal resistance to tetracycline and other antibiotics. J. Bacteriol. 155:541-548.

The invention will now be further described by way of the following non-limiting examples.

EXAMPLES

Example 1

Production and Genomic Analysis of Attenuated *S. suis*

In order to develop a broadly protective vaccine against *S. suis* infections, a US field strain (parent strain, Newport Laboratories no. 8-1433-1, SEQ ID NO:9) was isolated from a porcine brain swab. The isolate was identified as *S. suis* serotype 2, based on biochemical reactions and agglutination tests. Attenuation of this parent strain was accomplished by chemical mutagenesis using acriflavine hydrochloride, as described by Sinha et al. Briefly, the S. suis parent cells were grown for 18 hours in trypticase soy broth containing 5% sheep blood supplemented with 10 µM/ml acriflavine hydrochloride. The surviving cells were re-isolated on sheep blood agar plates. Twenty individual colonies were selected and grown separately in the same liquid media. One culture out of the 20 was selected and injected ($1.76 \times 10^9$ cells/ml) into pigs to determine virulence. Ten pigs were inoculated, orally, and observed for 26 days. Clinical signs consistent to S. suis infection were not observed in this time period. In addition to being highly attenuated, the mutant strain was resistant to neomycin. Furthermore, the whole genome of the mutant/candidate vaccine strain (SEQ ID NO:10), as well as the parent strain (SEQ ID NO:9), was completely sequenced and analyzed for single nucleotide polymorphisms (SNPs) which may confer the avirulent phenotype.

Sequencing. To sequence the genomes of the parental and mutant strains, log phase cultures of S. suis were pelleted and DNA was purified using Qiagen DNA mini kit (Qiagen, Valencia, Calif.). A genomic DNA library was then produced (Illumina Genomic DNA Prep Kit, Illumina, San Diego, Calif.), and subjected to cluster amplification on a Single End Flow Cell v4 with a Cluster Generation Station instrument (Illumina) to generate raw cluster intensity of ~600,000 mm$^2$. Sequencing was performed on a Genome Analyzer GAII for 56 cycles using Sequencing Kit reagents (Illumina). The sequences were then compared against the reported GenBank genome sequence of S. suis, P1/7 AM946016.1 (SEQ ID NO:11), and homology was identified with known defined genes. The sequences of both the parent and mutant strains were compared to look for single nucleotide polymorphisms (SNPs) that occurred in the coding regions of the genes (though it is acknowledged and envisioned by inventors non-coding regions may also be responsible for the attenuated/avirulent phenotypes). This analysis revealed several SNPs and those that resulted in the amino acid changes (non-synonymous) were subjected to further verification. The SNPs that resulted in the amino acid change were verified using Sanger Sequencing technique according to established protocols.

Reads were filtered for quality using a custom Python script. Low quality bases were first trimmed from the ends of the reads, after which they were then only kept if there were at least 40 bp with quality >20 and no ambiguously called internal bases. Following the trimming and filtering step reads were mapped against a set of reference genomes using the Burrows-Wheeler Aligner (BWA) version 0.6.1-r104. The Sequence Alignment/Map (SAM) output of BWA was then further analyzed using the SAMtools package (sourceforge webpages) in order to call variants. The resulting variant calls were then further analyzed using a custom script written in R in which variants were annotated based on their position within the genome. Variants were also filtered based on depth of coverage, the genotype quality reported by SAMtools, and for variants which were segregating with respect to samples from parent and mutant. SAMtools was also used to generate a consensus sequences based on the mapping results. This sequence was annotated based on the reference sequence and formatted as a Genbank file for Artemis compatibility using custom scripts and BioPython (Biophython web pages). Comparison of the parent vs. mutant (vaccine) genomes resulted in 3 SNPs spanning across two genes; 1) Two SNPs in rpsL-S12 a 30S ribosomal subunit protein and 2) One SNP in ABC transporter ATP binding membrane protein. These three SNPs were confirmed by standard Sanger sequencing methods.

Functional significance of rpsL-S12 a 30S ribosomal subunit protein: The small, 30S subunit proteins (S) and the large 50S subunit proteins (L) are critical components of protein synthesis machinery. These subunit proteins function as binding sites for many antibiotics and mutations in any one/more of these subunit proteins result in antibiotic resistance or susceptibility. Mutations caused by single nucleotide polymorphisms (SNPs) in the smaller subunit confer resistance to antibiotics such as tetracycline, spectinomycin, hygromycin B and streptomycin, whereas mutations in the larger subunit confer resistance against chloramphenicol, erythromycin, and strepgramin B. The S. suis vaccine strain is resistant to neomycin (16 µg/ml) as a result of these two SNPs in the small ribosomal subunit protein (S12) and has a avirulent phenotype. In wild type bacteria, neomycin is actively transported across the bacterial cell membrane, binds to a specific receptor protein on the 30S subunit of bacterial ribosomes, and interferes with an initiation complex between mRNA (messenger RNA) and the 30S subunit, inhibiting protein synthesis. DNA may be misread, thus producing nonfunctional proteins; polyribosomes are split apart and are unable to synthesize protein [McEvoy, 1989].

Functional significance of ABC transporter ATP binding membrane protein: Bacterial ATP-binding cassette transporters (ABC-transporter) are essential for cell survival and to transport virulence or virulence associated factors [Davidson et al., 2008; Henderson et al., 1994]. ABC transporters are extremely vital in cell survival and they function as osmoprotectants by mediating uptake of solutes and prevent lethal increase in osmotic strength [Poolman et al., 2004]. Furthermore, bacterial ABC proteins are also involved in the regulation of several physiological processes. ABC-transporters also serve in bacterial efflux systems by extruding components to the cell surface (e.g. capsular polysaccharides, lipopolysaccharides, and teichoic acid), proteins involved in bacterial pathogenesis (e.g. hemolysis, heme-binding protein, and alkaline protease), heme, hydrolytic enzymes, S-layer proteins, competence factors, toxins, antibiotics, bacteriocins, peptide antibiotics, drugs and siderophores [Davidson et al., 2008; Davidson and Chen, 2004]. They also play important roles in biosynthetic pathways, including extracellular polysaccharide biosynthesis and cytochrome biogenesis [Zhou et al., 1998; Poole et al., 1994].

Functional significance of marR transcription regulator. NCBI conserved domain analysis indicates that this gene encodes a transcriptional regulator containing "helix-turn-helix" motif involved in multiple antibiotic resistance (HTH_MARR), part of the marRAB operon. In *Escherichia coli*, marA encodes a positive regulator of the antibiotic resistance response, whereas marR encodes a repressor of marRAB transcription and controls the production of MarA in response to environmental signals (George and Levy, 1983). The SNP in the disclosed vaccine strain lies within the HTH_MARR domain (amino acid positions 30 to 125). The helix-turn-helix domain binds to DNA and is the hall mark feature of transcription regulators. The wild type MarR protein is a dimer with each subunit containing a winged-helix DNA binding motif involved in regulating transcription.

Taken together, mutations in these three genes (SNPs summarized in Table 1) make NPL S. suis vaccine strain avirulent and resistant to neomycin, and possibly other antibiotics.

TABLE 1

Location of SNPs and identification of mutated genes in the attenuated *S. suis* strain

| Gene | SNP # | Nuc Position | Parent Strain | Vaccine Strain | Amino acid change |
|---|---|---|---|---|---|
| rpsL-S12 | 1 | 167 | A (found in SEQ ID NO: 1) | C (found in SEQ ID NO: 3) | Lysine to Threonine (K-T) |
| rpsL-S12 | 2 | 301 | A (found in SEQ ID NO: 1) | C (found in SEQ ID NO: 3) | Lysine to Glutamine (K-Q) |
| ABC Transporter ATP bmp | 3 | 323 | G (found in SEQ ID NO: 5) | A (found in SEQ ID NO: 7) | Arginine to Histidine (R-H) |
| marR Transcription Regulator | 4 | 265 | C (found in SEQ ID NO: 9) | T (found in SEQ ID NO: 11) | Arginine to Cysteine (R-C) |

Example 2

Efficacy of Attenuated *S. suis* Vaccines in Porcine

General Protocol for Efficacy Studies: Colony forming units (CFUs) per milliliter of each vaccine dilution were determined through titration prior to and following vaccination.

All pigs enrolled in these studies were obtained from Midwest Research Swine, Gibbon, MN, and were healthy and normal at time of delivery. The herd is considered a high health source herd which did not have a history of *Streptococcus suis* infection and was negative for Porcine Reproductive and Respiratory Syndrome Virus (PRRSV). The source herd piglets had a history of being susceptible to *S. suis* challenge in previous studies. Pigs were received at 17-24 days of age. Animals were observed prior to vaccination and were deemed clinically normal as they lacked signs of disease, including coughing, abdominal breathing, and/or lameness. The individual pig was used as the experimental unit in these studies and ear tagged prior to delivery. Pigs were randomly assigned to rooms and to treatment groups using the random number generator in Microsoft Excel.

Schedule of events. All pigs were vaccinated on day 0. Each pig in the vaccine groups received 1 mL of appropriate vaccine, orally. Control animals were administered 1 mL of sterile saline, orally, which served as the placebo. Approximately 30-35 days following vaccination, all pigs were challenged and observed for eleven days following challenge.

Challenge. The challenge isolate was from a brain swab sample (isolate 8-1433-1). It was identified as a *Streptococcus suis* type 2 isolate through colony appearance on blood agar plates (small, white, smooth, round colonies), Grams stain reaction, biochemical testing (alpha-hemolytic, catalase negative, no growth in broth with 6.5% sodium chloride, and esculin positive). The isolate was grown to approximately 9 logs/mL in a liquid culture media, frozen in 1 mL aliquots in sterile ampules labeled "8-1433-1", and stored at −80° C. Previous studies demonstrated virulence of this isolate in pigs.

Approximately 4 hours prior to challenge, an ampule of the virulent type 2 *Streptococcus suis* field isolate (isolate 8-1433-1) was thawed. The ampule was used to inoculate fresh media and this culture was incubated on an orbital shaker at 37° C. until it reached an optical density of approximately 1.0 at 600 nanometers (nm) on a spectrophotometer. The culture was Gram stained; characteristic colonies of small cocci in chains and single cells were present and pure. The viable count of the challenge inoculum was determined immediately prior to and immediately following challenge. Each pig received 2 mL of the challenge inoculum intramuscularly.

Observations. Pigs were observed daily by individuals who were blinded to treatment allocation. Any animals exhibiting lameness, reluctance to rise, central nervous system (CNS) disorders, or death were recorded. "*S. suis* DMO" is the attenuated strain comprising the SNPs recited in Table 1, which was deposited in accordance with the Budapest Treaty under ATCC Patent Deposit Designation PTA-13269.

TABLE 2

Oral Route Vx/Challenge Study 1

| Treatment Group | Percent Diseased | Percent Dead | Percent Protection |
|---|---|---|---|
| 6 logs, DMO | 50% | 30% | 70% |
| 7 logs, DMO | 30% | 10% | 90% |
| 8 logs, DMO | 44% | 11% | 89% |
| Controls | 90% | 40% | 60% |

TABLE 3

Oral Route Vx/Challenge Study 1

| Treatment Group | Percent Diseased | Percent Dead | Percent Protection |
|---|---|---|---|
| *S. suis* DMO | 40% | 30% | 70% |
| Controls | 80% | 40% | 60% |

TABLE 4

Oral Route Vx/Challenge Study 2

| Treatment Group | Percent Diseased | Percent Dead | Percent Protection |
|---|---|---|---|
| 6 logs, DMO | 15% | 10% | 90% |
| 7 logs, DMO | 10.5% | 5.2% | 94.8% |
| 8 logs, DMO | 10.5% | 10.5% | 89.5% |
| Controls | 60% | 33.3% | 66.7% |

TABLE 5

Efficacy Study 1

| Group | # dead | % dead | # diseased | % diseased |
|---|---|---|---|---|
| 6 logs, DMO | 6/20 | 30% | 9/20 | 45% |
| 7 logs, DMO | 0/20 | 0% | 4/20 | 20% |
| 8 logs, DMO | 3/20 | 15% | 6/20 | 30% |
| Controls | 6/20 | 30% | 11/20 | 55% |

TABLE 6

Efficacy Study 2

| Group | # dead | % dead | # diseased | % diseased |
|---|---|---|---|---|
| 6 logs, DMO | 8/20 | 40% | 12/20 | 60.0% |
| 7 logs, DMO | 4/19 | 21.1% | 11/19 | 58.0% |
| 8 logs, DMO | 5/20 | 25.0% | 5/20 | 25.0% |
| Controls | 10/19 | 52.6% | 16/19 | 84.0% |

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. An attenuated *Streptococcus suis* (*S. suis*) vaccine strain capable of providing a safe and protective immune response in porcine against *S. suis* or diseases caused by *S. suis*;
    wherein the strain comprises one or more virulence gene(s), coding for polypeptide(s) having one or more amino acid substitutions relative to the corresponding polypeptide(s) in the strain's corresponding virulent parental *S. suis* strain; and
    wherein the genes are rpsL-S12 (a $_{30}$S ribosomal subunit protein), an ABC transporter ATP binding membrane protein (ABC-ATPBMP), marR transcription regulator, or combinations thereof.

2. The vaccine strain of claim 1, comprising nucleic acid sequences as set forth in SEQ ID NOs:3, 7and 11.

3. The vaccine strain of claim 1, wherein the level(s) of the peptide(s) expressed by the rpsL-S12, the ABC-ATPBMP, marR, or combinations thereof, is reduced relative to the parent *S. suis* strain, which expresses rpsL-S12, ABC-ATPBMP, and marR peptides having the sequence as set forth in SEQ ID NOs:2 (rpsL-S12), 6 (ABC-ATPBMP), and 10 (marR).

4. The vaccine strain of claim 1, characterized in that it comprises nucleic acids sequences having a C in a position corresponding to nucleotide 167 of SEQ ID NO:3; a C in a position corresponding to nucleotide 301 of SEQ ID NO:3; an A in a position corresponding to nucleotide 323 of SEQ ID NO:7; and a T in a position corresponding to nucleotide 265 of SEQ ID NO:11.

5. The vaccine strain of claim 4, characterized in that it is the strain deposited at the ATCC under the Patent Deposit Designation PTA-13269.

6. A vaccine composition comprising the attenuated vaccine strain of claim 1, and a pharmaceutically or veterinarily acceptable vehicle, diluent or excipient.

7. The vaccine composition of claim 6, further comprising an adjuvant.

8. The vaccine composition of claim 7, wherein the adjuvant is selected from chitosan, methylated chitosan, trimethylated chitosan and combinations thereof.

9. The vaccine composition of claim 8, wherein the adjuvant is chitosan.

10. The vaccine composition of claim 7, wherein the adjuvant is inactivated bacteria, inactivated virus, fractions of inactivated bacteria, bacterial lipopolysaccharides, bacterial toxins, or derivatives or combinations thereof.

11. The vaccine composition of claim 10, further comprising at least one additional antigen.

12. The vaccine composition of claim 11, wherein the at least one additional antigens is capable of eliciting in a porcine an immune response against M. hyo, PCV2, PRRSV or SIV.

* * * * *

SEQUENCE LISTING

<160> NUMBER OF SEQ ID NOS: 12

<210> SEQ ID NO 1
<211> LENGTH: 411
<212> TYPE: DNA
<213> ORGANISM: Streptococcus suis

<400> SEQUENCE: 1

```
atgcctacaa ttaaccagtt ggtacgtaaa ccacgtaagt ctaaagtaga aaaatctaaa      60
tcaccagctt tgaacgttgg ttacaacagc cgtaaaaaag ttcaaacaaa cgtttcatca     120
ccacaaaaac gcggtgttgc aactcgtgtc ggaacaatga cacctaaaaa acctaactca     180
gcccttcgta aatttgctcg tgtacgtttg agcaacctta tcgaagttac tgcttacatc     240
ccaggtatcg gtcacaactt gcaagaacac agtgtggttc ttcttcgtgg tggacgtgta     300
aaagaccttc caggggtacg ttaccatatc gttcgtggtg cacttgatac tgctggtgta     360
aacgatcgta agcaaggccg ttctaaatac ggtactaaac gtccaaaagg c              411
```

<210> SEQ ID NO 2
<211> LENGTH: 137
<212> TYPE: PRT
<213> ORGANISM: Streptococcus suis

<400> SEQUENCE: 2

```
Met Pro Thr Ile Asn Gln Leu Val Arg Lys Pro Arg Lys Ser Lys Val
1               5                   10                  15

Glu Lys Ser Lys Ser Pro Ala Leu Asn Val Gly Tyr Asn Ser Arg Lys
            20                  25                  30

Lys Val Gln Thr Asn Val Ser Ser Pro Gln Lys Arg Gly Val Ala Thr
        35                  40                  45

Arg Val Gly Thr Met Thr Pro Lys Lys Pro Asn Ser Ala Leu Arg Lys
    50                  55                  60

Phe Ala Arg Val Arg Leu Ser Asn Leu Ile Glu Val Thr Ala Tyr Ile
65                  70                  75                  80

Pro Gly Ile Gly His Asn Leu Gln Glu His Ser Val Val Leu Leu Arg
                85                  90                  95

Gly Gly Arg Val Lys Asp Leu Pro Gly Val Arg Tyr His Ile Val Arg
            100                 105                 110

Gly Ala Leu Asp Thr Ala Gly Val Asn Asp Arg Lys Gln Gly Arg Ser
```

```
            115                 120                 125
Lys Tyr Gly Thr Lys Arg Pro Lys Gly
    130                 135

<210> SEQ ID NO 3
<211> LENGTH: 411
<212> TYPE: DNA
<213> ORGANISM: Streptococcus suis

<400> SEQUENCE: 3
atgcctacaa ttaaccagtt ggtacgtaaa ccacgtaagt ctaaagtaga aaatctaaa       60 tcaccagctt tgaacgttgg ttacaacagc cgtaaaaaag ttcaaacaaa cgtttcatca     120
ccacaaaaac gcggtgttgc aactcgtgtc ggaacaatga cacctacaaa acctaactca     180
gcccttcgta aatttgctcg tgtacgtttg agcaacctta tcgaagttac tgcttacatc     240
ccaggtatcg gtcacaactt gcaagaacac agtgtggttc ttcttcgtgg tggacgtgta     300
caagaccttc caggggtacg ttaccatatc gttcgtggtg cacttgatac tgctggtgta     360
aacgatcgta agcaaggccg ttctaaatac ggtactaaac gtccaaaagg c               411

<210> SEQ ID NO 4
<211> LENGTH: 137
<212> TYPE: PRT
<213> ORGANISM: Streptococcus suis

<400> SEQUENCE: 4

Met Pro Thr Ile Asn Gln Leu Val Arg Lys Pro Arg Lys Ser Lys Val
1               5                   10                  15

Glu Lys Ser Lys Ser Pro Ala Leu Asn Val Gly Tyr Asn Ser Arg Lys
            20                  25                  30

Lys Val Gln Thr Asn Val Ser Ser Pro Gln Lys Arg Gly Val Ala Thr
        35                  40                  45

Arg Val Gly Thr Met Thr Pro Thr Lys Pro Asn Ser Ala Leu Arg Lys
    50                  55                  60

Phe Ala Arg Val Arg Leu Ser Asn Leu Ile Glu Val Thr Ala Tyr Ile
65                  70                  75                  80

Pro Gly Ile Gly His Asn Leu Gln Glu His Ser Val Val Leu Leu Arg
                85                  90                  95

Gly Gly Arg Val Gln Asp Leu Pro Gly Val Arg Tyr His Ile Val Arg
            100                 105                 110

Gly Ala Leu Asp Thr Ala Gly Val Asn Asp Arg Lys Gln Gly Arg Ser
        115                 120                 125

Lys Tyr Gly Thr Lys Arg Pro Lys Gly
    130                 135

<210> SEQ ID NO 5
<211> LENGTH: 1782
<212> TYPE: DNA
<213> ORGANISM: Streptococcus suis

<400> SEQUENCE: 5
atgaagacgt tacgtttttt ctggttttat tttaaacgct ataaactgtc ctttgctgtg       60 attttctag ccattgtggc agcgacctac ctgcaggtta agacacctgt tttccttgga      120
aatgccattg cggagatggg gaaaatcggg caggcttact ttatggccaa tcaagctggt     180
caggctgact ttcagccaga catggctgat tttaacgggg ttatgctcaa tctttttcttt    240 gcctatgcgg cgacggttgt ggcttccttg atttacactc tcctcttcac gcgtatcgtg     300
```

```
gctcattcga ccaaccgtat gcgtaagggc ttgtttggca aactggaacg cttgacagtt    360
gccttctttg atagccacaa ggacggggat atactttctc gctttaccag tgatttggac    420
aatatccaaa acgctttcaa ccagtccttg acccaagtgg tgaccaacat cgctctttat    480
gttggtatgg tcatcatgat gttccgtcag gatactcgct tggccttggt gaccattgct    540
tctacgccag ttgccttgat tgccttggtc gttatcatcc gcctatcacg gaaatatacg    600
gataagcaac aggctgcggt gtctaaactc aatgcctaca tggacgagaa aatttctgga    660
caaaaagcga ttattgtaca aggtgtgcag gaagagacaa ttgatggttt cttggagctc    720
aatgaagaag ttcgtcgcac aactttcaag ggacgcttgt tggtgggat tctcttccca    780
tttatgaatg gtatgagttt ggtcaatacg gccattgtta tctttgcagg ttccagcatt    840
gttctcaatg acagctcact ggaaacagct gccgcacttg gtctggtggt gacttttgtt    900
caatactcgc aacagtatta ccagccaatc atgcaggttg ctgccagctg gcagaattg    960
cagctagctt tcacaggagc tcatcgtatt caggaaatgt tgatgagcc tgaggaagtt   1020
cgtcctcaaa acgctccgct atttaccgaa ttaaaagaag gtgttgaaat taaggacatc   1080
gactttggct acttgccagg tcagaaggtc ttggacaagg tgtctatctc tgctcctaag   1140
ggtaagatgg tggcggtcgt tggtccgacg ggatctggta agactaccat tatgaacttg   1200
attaaccgct ctacgatgt caatggtggt agtgtggcct tgatggtcg cgatattcgg   1260
gaatatgatt tggatagctt gcggaataag gtcggtatcg tcttgcagga gtcggtgtta   1320
ttctcgggta ctattgcgga caatattcgc tttggtgatg agagcatttc gcaggaaatg   1380
gtggaaaccg cagctcgtgc cacccatatc cacgacttca tcatgagctt gccagagggc   1440
tatgaaacct ttgtgaccga tgatgagaat gtcttctcaa caggtcagaa acagttgatt   1500
tccattgccc gtacgctttt gacagaccca caagtcttga ttttggacga agcaacctca   1560
aacgttgata ccgtaacgga ggccaaaatt caaaaggcta tggaggccat atcgcagga   1620
cggactagct tcgtcattgc ccaccgcctc aaaaccattc tcaatgcgga tgaaatcatc   1680
gtcctcaagg atggaaaggt tatcgagcaa ggcaaccaca gccaacttct caaactaaat   1740
ggcttctacg ccgaacttta ccacaaccag tttgtgtttg aa                      1782
```

<210> SEQ ID NO 6
<211> LENGTH: 594
<212> TYPE: PRT
<213> ORGANISM: Streptococcus suis

<400> SEQUENCE: 6

```
Met Lys Thr Leu Arg Phe Phe Trp Phe Tyr Phe Lys Arg Tyr Lys Leu
1               5                   10                  15

Ser Phe Ala Val Ile Phe Leu Ala Ile Val Ala Ala Thr Tyr Leu Gln
            20                  25                  30

Val Lys Thr Pro Val Phe Leu Gly Asn Ala Ile Ala Glu Met Gly Lys
        35                  40                  45

Ile Gly Gln Ala Tyr Phe Met Ala Asn Gln Ala Gly Gln Ala Asp Phe
    50                  55                  60

Gln Pro Asp Met Ala Asp Phe Asn Gly Val Met Leu Asn Leu Phe Phe
65                  70                  75                  80

Ala Tyr Ala Ala Thr Val Val Ala Ser Leu Ile Tyr Thr Leu Leu Phe
                85                  90                  95

Thr Arg Ile Val Ala His Ser Thr Asn Arg Met Arg Lys Gly Leu Phe
            100                 105                 110
```

```
Gly Lys Leu Glu Arg Leu Thr Val Ala Phe Phe Asp Ser His Lys Asp
            115                 120                 125

Gly Asp Ile Leu Ser Arg Phe Thr Ser Asp Leu Asp Asn Ile Gln Asn
        130                 135                 140

Ala Phe Asn Gln Ser Leu Thr Gln Val Val Thr Asn Ile Ala Leu Tyr
145                 150                 155                 160

Val Gly Met Val Ile Met Met Phe Arg Gln Asp Thr Arg Leu Ala Leu
                165                 170                 175

Val Thr Ile Ala Ser Thr Pro Val Ala Leu Ile Ala Leu Val Val Ile
            180                 185                 190

Ile Arg Leu Ser Arg Lys Tyr Thr Asp Lys Gln Gln Ala Ala Val Ser
        195                 200                 205

Lys Leu Asn Ala Tyr Met Asp Glu Lys Ile Ser Gly Gln Lys Ala Ile
210                 215                 220

Ile Val Gln Gly Val Gln Glu Thr Ile Asp Gly Phe Leu Glu Leu
225                 230                 235                 240

Asn Glu Glu Val Arg Arg Thr Thr Phe Lys Gly Arg Leu Phe Gly Gly
                245                 250                 255

Ile Leu Phe Pro Phe Met Asn Gly Met Ser Leu Val Asn Thr Ala Ile
            260                 265                 270

Val Ile Phe Ala Gly Ser Ser Ile Val Leu Asn Asp Ser Ser Leu Glu
        275                 280                 285

Thr Ala Ala Leu Gly Leu Val Val Thr Phe Val Gln Tyr Ser Gln
290                 295                 300

Gln Tyr Tyr Gln Pro Ile Met Gln Val Ala Ala Ser Trp Ala Glu Leu
305                 310                 315                 320

Gln Leu Ala Phe Thr Gly Ala His Arg Ile Gln Glu Met Phe Asp Glu
                325                 330                 335

Pro Glu Glu Val Arg Pro Gln Asn Ala Pro Leu Phe Thr Glu Leu Lys
            340                 345                 350

Glu Gly Val Glu Ile Lys Asp Ile Asp Phe Gly Tyr Leu Pro Gly Gln
        355                 360                 365

Lys Val Leu Asp Lys Val Ser Ile Ser Ala Pro Lys Gly Lys Met Val
370                 375                 380

Ala Val Val Gly Pro Thr Gly Ser Gly Lys Thr Thr Ile Met Asn Leu
385                 390                 395                 400

Ile Asn Arg Phe Tyr Asp Val Asn Gly Gly Ser Val Ala Phe Asp Gly
                405                 410                 415

Arg Asp Ile Arg Glu Tyr Asp Leu Asp Ser Leu Arg Asn Lys Val Gly
            420                 425                 430

Ile Val Leu Gln Glu Ser Val Leu Phe Ser Gly Thr Ile Ala Asp Asn
        435                 440                 445

Ile Arg Phe Gly Asp Glu Ser Ile Ser Gln Glu Met Val Glu Thr Ala
450                 455                 460

Ala Arg Ala Thr His Ile His Asp Phe Ile Met Ser Leu Pro Glu Gly
465                 470                 475                 480

Tyr Glu Thr Phe Val Thr Asp Asp Glu Asn Val Phe Ser Thr Gly Gln
                485                 490                 495

Lys Gln Leu Ile Ser Ile Ala Arg Thr Leu Leu Thr Asp Pro Gln Val
            500                 505                 510

Leu Ile Leu Asp Glu Ala Thr Ser Asn Val Asp Thr Val Thr Glu Ala
        515                 520                 525
```

```
Lys Ile Gln Lys Ala Met Glu Ala Ile Ile Ala Gly Arg Thr Ser Phe
    530             535                 540
Val Ile Ala His Arg Leu Lys Thr Ile Leu Asn Ala Asp Glu Ile Ile
545                 550                 555                 560
Val Leu Lys Asp Gly Lys Val Ile Glu Gln Gly Asn His Ser Gln Leu
                565                 570                 575
Leu Lys Leu Asn Gly Phe Tyr Ala Glu Leu Tyr His Asn Gln Phe Val
            580                 585                 590
Phe Glu

<210> SEQ ID NO 7
<211> LENGTH: 1782
<212> TYPE: DNA
<213> ORGANISM: Streptococcus suis

<400> SEQUENCE: 7
atgaagacgt tacgtttttt ctggttttat tttaaacgct ataaactgtc ctttgctgtg      60
attttctag ccattgtggc agcgacctac ctgcaggtta agacacctgt tttccttgga     120
aatgccattg cggagatggg gaaaatcggg caggcttact ttatggccaa tcaagctggt     180
caggctgact ttcagccaga catggctgat tttaacgggg tatgctcaa tcttttcttt     240
gcctatgcgg cgacggttgt ggcttccttg atttacactc tcctcttcac gcgtatcgtg     300
gctcattcga ccaaccgtat gcataagggc ttgtttggca aactggaacg cttgacagtt     360
gccttctttg atagccacaa ggacggggat atactttctc gctttaccag tgatttggac     420
aatatccaaa acgctttcaa ccagtccttg acccaagtgg tgaccaacat cgctctttat     480
gttggtatgg tcatcatgat gttccgtcag gatactcgct tggccttggt gaccattgct     540
tctacgccag ttgccttgat tgccttggtc gttatcatcc gcctatcacg gaaatatacg     600
gataagcaac aggctgcggt gtctaaactc aatgcctaca tggacgagaa atttctggga     660
caaaaagcga ttattgtaca aggtgtgcag gaagagacaa ttgatggttt cttggagctc     720
aatgaagaag ttcgtcgcac aactttcaag ggacgcttgt ttggtgggat tctcttccca     780
tttatgaatg gtatgagttt ggtcaatacg gccattgtta tctttgcagg ttccagcatt     840
gttctcaatg acagctcact ggaaacagct gccgcacttg gtctggtggt gacttttgtt     900
caatactcgc aacagtatta ccagccaatc atgcaggttg ctgccagctg gcagaattg     960
cagctagctt tcacaggagc tcatcgtatt caggaaatgt tgatgagcc tgaggaagtt    1020
cgtcctcaaa acgctccgct atttaccgaa ttaaaagaag tgttgaaat taaggacatc    1080
gactttggct acttgccagg tcagaaggtc ttggacaagg tgtctatctc tgctcctaag    1140
ggtaagatgg tggcggtcgt tggtccgacg ggatctggta agactaccat tatgaacttg    1200
attaaccgct tctacgatgt caatggtggt agtgtggcct tgatggtcg cgatattcgg    1260
gaatatgatt tggatagctt gcggaataag gtcggtatcg tcttgcagga gtcggtgtta    1320
ttctcgggta ctattgcgga caatattcgc tttggtgatg agagcatttc gcaggaaatg    1380
gtggaaaccg cagctcgtgc cacccatatc cacgacttca tcatgagctt gccagagggc    1440
tatgaaacct ttgtgaccga tgatgagaat gtcttctcaa caggtcagaa acagttgatt    1500
tccattgccc gtacgctttt gacagaccca caagtcttga ttttggacga agcaacctca    1560
aacgttgata ccgtaacgga ggccaaaatt caaaaggcta tggaggccat tatcgcagga    1620
cggactagct tcgtcattgc ccaccgcctc aaaaccattc tcaatgcgga tgaaatcatc    1680
gtcctcaagg atggaaaggt tatcgagcaa ggcaaccaca gccaacttct caaactaaat    1740
```
ggcttctacg ccgaacttta ccacaaccag tttgtgtttg aa          1782

<210> SEQ ID NO 8
<211> LENGTH: 594
<212> TYPE: PRT
<213> ORGANISM: Streptococcus suis

<400> SEQUENCE: 8

Met Lys Thr Leu Arg Phe Phe Trp Phe Tyr Phe Lys Arg Tyr Lys Leu
1               5                   10                  15

Ser Phe Ala Val Ile Phe Leu Ala Ile Val Ala Ala Thr Tyr Leu Gln
            20                  25                  30

Val Lys Thr Pro Val Phe Leu Gly Asn Ala Ile Ala Glu Met Gly Lys
        35                  40                  45

Ile Gly Gln Ala Tyr Phe Met Ala Asn Gln Ala Gly Gln Ala Asp Phe
    50                  55                  60

Gln Pro Asp Met Ala Asp Phe Asn Gly Val Met Leu Asn Leu Phe Phe
65                  70                  75                  80

Ala Tyr Ala Ala Thr Val Val Ala Ser Leu Ile Tyr Thr Leu Leu Phe
                85                  90                  95

Thr Arg Ile Val Ala His Ser Thr Asn Arg Met His Lys Gly Leu Phe
            100                 105                 110

Gly Lys Leu Glu Arg Leu Thr Val Ala Phe Phe Asp Ser His Lys Asp
        115                 120                 125

Gly Asp Ile Leu Ser Arg Phe Thr Ser Asp Leu Asp Asn Ile Gln Asn
    130                 135                 140

Ala Phe Asn Gln Ser Leu Thr Gln Val Val Thr Asn Ile Ala Leu Tyr
145                 150                 155                 160

Val Gly Met Val Ile Met Met Phe Arg Gln Asp Thr Arg Leu Ala Leu
                165                 170                 175

Val Thr Ile Ala Ser Thr Pro Val Ala Leu Ile Ala Leu Val Val Ile
            180                 185                 190

Ile Arg Leu Ser Arg Lys Tyr Thr Asp Lys Gln Gln Ala Ala Val Ser
        195                 200                 205

Lys Leu Asn Ala Tyr Met Asp Glu Lys Ile Ser Gly Gln Lys Ala Ile
    210                 215                 220

Ile Val Gln Gly Val Gln Glu Glu Thr Ile Asp Gly Phe Leu Glu Leu
225                 230                 235                 240

Asn Glu Glu Val Arg Arg Thr Thr Phe Lys Gly Arg Leu Phe Gly Gly
                245                 250                 255

Ile Leu Phe Pro Phe Met Asn Gly Met Ser Leu Val Asn Thr Ala Ile
            260                 265                 270

Val Ile Phe Ala Gly Ser Ser Ile Val Leu Asn Asp Ser Ser Leu Glu
        275                 280                 285

Thr Ala Ala Ala Leu Gly Leu Val Val Thr Phe Val Gln Tyr Ser Gln
    290                 295                 300

Gln Tyr Tyr Gln Pro Ile Met Gln Val Ala Ala Ser Trp Ala Glu Leu
305                 310                 315                 320

Gln Leu Ala Phe Thr Gly Ala His Arg Ile Gln Glu Met Phe Asp Glu
                325                 330                 335

Pro Glu Glu Val Arg Pro Gln Asn Ala Pro Leu Phe Thr Glu Leu Lys
            340                 345                 350

Glu Gly Val Glu Ile Lys Asp Ile Asp Phe Gly Tyr Leu Pro Gly Gln
        355                 360                 365

Lys Val Leu Asp Lys Val Ser Ile Ser Ala Pro Lys Gly Lys Met Val
            370                 375                 380

Ala Val Val Gly Pro Thr Gly Ser Gly Lys Thr Thr Ile Met Asn Leu
385                 390                 395                 400

Ile Asn Arg Phe Tyr Asp Val Asn Gly Ser Val Ala Phe Asp Gly
            405                 410                 415

Arg Asp Ile Arg Glu Tyr Asp Leu Asp Ser Leu Arg Asn Lys Val Gly
            420                 425                 430

Ile Val Leu Gln Glu Ser Val Leu Phe Ser Gly Thr Ile Ala Asp Asn
            435                 440                 445

Ile Arg Phe Gly Asp Glu Ser Ile Ser Gln Glu Met Val Glu Thr Ala
            450                 455                 460

Ala Arg Ala Thr His Ile His Asp Phe Ile Met Ser Leu Pro Glu Gly
465                 470                 475                 480

Tyr Glu Thr Phe Val Thr Asp Asp Glu Asn Val Phe Ser Thr Gly Gln
            485                 490                 495

Lys Gln Leu Ile Ser Ile Ala Arg Thr Leu Leu Thr Asp Pro Gln Val
            500                 505                 510

Leu Ile Leu Asp Glu Ala Thr Ser Asn Val Asp Thr Val Thr Glu Ala
            515                 520                 525

Lys Ile Gln Lys Ala Met Glu Ala Ile Ile Ala Gly Arg Thr Ser Phe
            530                 535                 540

Val Ile Ala His Arg Leu Lys Thr Ile Leu Asn Ala Asp Glu Ile Ile
545                 550                 555                 560

Val Leu Lys Asp Gly Lys Val Ile Glu Gln Gly Asn His Ser Gln Leu
            565                 570                 575

Leu Lys Leu Asn Gly Phe Tyr Ala Glu Leu Tyr His Asn Gln Phe Val
            580                 585                 590

Phe Glu

<210> SEQ ID NO 9
<211> LENGTH: 447
<212> TYPE: DNA
<213> ORGANISM: Streptococcus suis

<400> SEQUENCE: 9
atgggacata ctattgcaga ttttcggaac ttgctcaatc agattgaaca aattagtgaa      60
accattgcaa agaatacga tgtggagcac ttggctggtc cacagggctg ggccttgcgc     120
ttcattgcgg aacggtcgga agccgaaacc tttgtaaaag atatagaagc ggaattaaag     180
atttccaaat cggttgccag caatctggtc aagagaatgg agaaaaatgg ctttatccaa     240
gtccttccct ctaaggttga caaacgcttc aaacagctgg ttttgacaga aagggacaa      300 gggaagatat gtcacctgaa agctttttcat gaagaaatgc accattcact tttttggggc     360
attcaaaaag aggactttga cttggttaaa caggtgggca atcaattaaa agtaaatatt     420
caacgctata aggagaagaa tcatgtt                                         447

<210> SEQ ID NO 10
<211> LENGTH: 149
<212> TYPE: PRT
<213> ORGANISM: Streptococcus suis

<400> SEQUENCE: 10

Met Gly His Thr Ile Ala Asp Phe Arg Asn Leu Leu Asn Gln Ile Glu
1               5                   10                  15

Gln Ile Ser Glu Thr Ile Ala Lys Glu Tyr Asp Val Glu His Leu Ala
            20                  25                  30

Gly Pro Gln Gly Trp Ala Leu Arg Phe Ile Ala Glu Arg Ser Glu Ala
        35                  40                  45

Glu Thr Phe Val Lys Asp Ile Glu Ala Glu Leu Lys Ile Ser Lys Ser
    50                  55                  60

Val Ala Ser Asn Leu Val Lys Arg Met Glu Lys Asn Gly Phe Ile Gln
65                  70                  75                  80

Val Leu Pro Ser Lys Val Asp Lys Arg Phe Lys Gln Leu Val Leu Thr
                85                  90                  95

Glu Lys Gly Gln Gly Lys Ile Cys His Leu Lys Ala Phe His Glu Glu
            100                 105                 110

Met His His Ser Leu Phe Trp Gly Ile Gln Lys Glu Asp Phe Asp Leu
        115                 120                 125

Val Lys Gln Val Gly Asn Gln Leu Lys Val Asn Ile Gln Arg Tyr Lys
    130                 135                 140

Glu Lys Asn His Val
145

<210> SEQ ID NO 11
<211> LENGTH: 447
<212> TYPE: DNA
<213> ORGANISM: Streptococcus suis

<400> SEQUENCE: 11
atgggacata ctattgcaga ttttcggaac ttgctcaatc agattgaaca aattagtgaa        60
accattgcaa agaatacga tgtggagcac ttggctggtc cacagggctg ggccttgcgc       120
ttcattgcgg aacggtcgga agccgaaacc tttgtaaaag atatagaagc ggaattaaag       180
atttccaaat cggttgccag caatctggtc aagagaatgg agaaaaatgg ctttatccaa       240
gtccttccct ctaaggttga caaatgcttc aaacagctgg ttttgacaga aagggacaa        300 gggaagatat gtcacctgaa agcttttcat gaagaaatgc accattcact ttttggggc        360 attcaaaaag aggactttga cttggttaaa caggtgggca atcaattaaa agtaaatatt       420
caacgctata aggagaagaa tcatgtt                                           447

<210> SEQ ID NO 12
<211> LENGTH: 149
<212> TYPE: PRT
<213> ORGANISM: Streptococcus suis

<400> SEQUENCE: 12

Met Gly His Thr Ile Ala Asp Phe Arg Asn Leu Leu Asn Gln Ile Glu
1               5                   10                  15

Gln Ile Ser Glu Thr Ile Ala Lys Glu Tyr Asp Val Glu His Leu Ala
            20                  25                  30

Gly Pro Gln Gly Trp Ala Leu Arg Phe Ile Ala Glu Arg Ser Glu Ala
        35                  40                  45

Glu Thr Phe Val Lys Asp Ile Glu Ala Glu Leu Lys Ile Ser Lys Ser
    50                  55                  60

Val Ala Ser Asn Leu Val Lys Arg Met Glu Lys Asn Gly Phe Ile Gln
65                  70                  75                  80

Val Leu Pro Ser Lys Val Asp Lys Cys Phe Lys Gln Leu Val Leu Thr
                85                  90                  95

Glu Lys Gly Gln Gly Lys Ile Cys His Leu Lys Ala Phe His Glu Glu

-continued

```
                100                  105                 110
Met His His Ser Leu Phe Trp Gly Ile Gln Lys Glu Asp Phe Asp Leu
            115                 120                 125

Val Lys Gln Val Gly Asn Gln Leu Lys Val Asn Ile Gln Arg Tyr Lys
    130                 135                 140

Glu Lys Asn His Val
145
```